United States Patent [19]

Umemura et al.

[11] 4,070,390

[45] Jan. 24, 1978

[54] METHOD FOR THE CATALYTICAL PREPARATION OF ACRYLONITRILE

[75] Inventors: Sumio Umemura; Kyoji Ohdan; Tokuo Matsuzaki; Taizo Uda; Mikio Hidaka; Yasuo Nakamura; Masao Tsuruoka, all of Ube, Japan

[73] Assignee: Ube Industries, Ltd., Ube, Japan

[21] Appl. No.: 732,361

[22] Filed: Oct. 14, 1976

[30] Foreign Application Priority Data

May 11, 1976 Japan .................................. 51-52832

[51] Int. Cl.² .......................................... C07C 120/14
[52] U.S. Cl. .................................. 260/465.3; 252/439
[58] Field of Search ..................................... 260/465.3

[56] References Cited

U.S. PATENT DOCUMENTS

| | | | |
|---|---|---|---|
| 3,471,545 | 10/1969 | Giordano et al. | 260/465.3 |
| 3,492,248 | 1/1970 | Notari et al. | 260/465.3 X |
| 3,641,102 | 2/1972 | Reulet et al. | 260/465.3 |
| 3,642,930 | 2/1972 | Grasselli et al. | 260/465.3 |
| 3,686,265 | 8/1972 | Reulet et al. | 260/465.3 |
| 3,766,092 | 10/1973 | Honda et al. | 260/465.3 X |
| 3,907,713 | 9/1975 | Grasselli et al. | 260/465.3 X |
| 3,907,859 | 9/1975 | Grasselli et al. | 260/465.3 |

FOREIGN PATENT DOCUMENTS

| | | | |
|---|---|---|---|
| 74 20,743 | 2/1975 | France | 260/465.3 |
| 933,493 | 8/1963 | United Kingdom | 260/465.3 |
| 1,025,676 | 4/1966 | United Kingdom | 260/465.3 |

*Primary Examiner*—Joseph P. Brust
*Attorney, Agent, or Firm*—Miller & Prestia

[57] ABSTRACT

Acrylonitrile can be produced in a high yield by the catalytical ammoxidation of propylene at an elevated temperature, preferably of 330° to 470° C, in the presence of a new type of catalyst consisting of an oxide composition of the empirical formula: $Mo_aCo_bFe_cBi_dX_eO_f$ wherein X denotes at least one atom of an element selected from vanadium and tellurium and wherein the ratio a:b:c:d:e:f is in a range of 10:3 to 10:1 to 7:0.1 to 0.7:0.01 to 1:34.6 to 54.1, said catalyst being prepared by providing an aqueous mixture containing molybdenum-, cobalt- and iron-containing compounds, bismuth-containing compound, and vanadium-or tellurium-containing compound, converting the aqueous mixture into a dried solid mixture and calcining the solid mixture at a temperature of at least 500° C.

27 Claims, No Drawings

METHOD FOR THE CATALYTICAL PREPARATION OF ACRYLONITRILE

The present invention relates to a method for the preparation of acrylonitrile. More particularly, the present invention relates to a method for the preparation of acrylonitrile by a catalytic ammoxidation of propylene in gas phase at an elevated temperature.

Various methods for the production of acrylonitrile by contacting propylene with oxygen and ammonia in gas phase in the presence of a catalyst at an elevated temperature are well-known as catalytical ammoxidation methods. Various types of catalysts are also provided for the above methods. The conventional types of catalysts consist mostly of oxide compositions which contain combinations of oxides of a plurality of elements. That is, Mo—Co—Fe—Bi—O type catalysts are known from Japanese Patent Application Laying-open No. 47-17718(1972) and Japanese Patent Application Laying-open No. 48-49719(1973). However, use of the Mo—Co—Fe—Bi—O types of catalysts in the production of acrylonitrile by the ammoxidation of propylene results in the following disadvantages wherein first, the yield of acrylonitrile calculated from the amount of propylene used is relatively low, that is, at maximum about 80%; secondly, in view of the relationship between the ammoxidation temperature and the yield of acrylonitrile, the optimum temperature at which acrylonitrile is produced in a highest yield is about 450° C which is relatively high and not preferable from the standpoint of industrial merit, and thirdly, in view of the relationship of the yield of acrylonitrile to the contact time of the reaction feed with the catalyst, the optimum contact time in which the yield of acrylonitrile is highest is undesirably and relatively long, and the space time yield of acrylonitrile, which term will be hereinafter defined, in the optimum contact time is low. In addition, the conventional types of catalysts have other disadvantages in that the cost of the catalysts is high because the catalysts contain therein relatively large amounts of bismuth which is expensive. The small content of bismuth in the conventional catalysts results in a low yield of acrylonitrile.

Under these circumstances, the inventors' aims were to provide a new type of catalyst capable of converting propylene into acrylonitrile in a high yield, at a relatively low reaction temperature, and during a relatively short contact time.

An object of the present invention is to provide a method for the catalytical preparation of acrylonitrile by ammoxidation of propylene, in the presence of a catalyst which allows acrylonitrile to be prepared in a high yield based on the amount of propylene used.

Another object of the present invention is to provide a method for the catalytical preparation of acrylonitrile by ammoxidation of propylene, in the presence of a catalyst which allows acrylonitrile to be prepared in a highest yield at a relatively low reaction temperature during a relatively short contact time.

A further object of the present invention is to provide a method for the catalytical preparation of acrylonitrile by ammoxidation of propylene, in the presence of a catalyst in a high space time yield of acrylonitrile.

Various studies have been carried out by the inventors of the present invention to attain the above-mentioned objects. As a result of their studies, the inventors have discovered that the above objects can be accomplished by employing a new type of catalyst which comprises a base catalytic component consisting of oxides of molybdenum, cobalt, iron and bismuth, and a small amount of an additional component consisting of at least one member selected from oxides of vanadium and tellurium, in an atomic ratio of the above-mentioned elements ranging within a specified scope. The present invention has been developed on the basis of the above-described discovery.

That is, the above-mentioned objects can be accomplished by the method of the present invention which comprises bringing a reaction feed containing propylene, ammonia and molecular oxygen in a gas phase into contact with a catalyst consisting of an oxide composition of the empirical formula:

wherein X represents at least one atom of an element selected from vanadium and tellurium; the subscripts $a$, $b$, $c$, $d$, $e$ and $f$, respectively denote the numbers of respective atoms of said elements, the ratio $a:b:c:d:e$ being in the range of 10:3 to 10:1 to 7:0.1 to 0.7:0.01 to 1; and the subscript denotes the number of oxygen atoms which satisfies the average valency of the elements, and the ratio $a:f$ being in the range of 10:34.6 to 54.1. Preferably, the ratio $a:b:c:d:e$ is in the range of 10:4 to 9:1.5 to 5:0.15 to 0.5:0.03 to 0.5.

The present invention is characterized by using the new type of catalyst mentioned above.

The utilization of the catalyst in accordance with the present invention results in the following technical merits.

1. In comparison with the conventional method using the old Mo—Co—Fe—Bi—O type catalyst, the method of the present invention can produce acrylonitrile in a high yield based on the amount of propylene used. When the method of the present invention is carried out under optimum conditions, it is possible to produce acrylonitrile in a yield of 80% or more.

2. The optimum reaction temperature at which acrylonitrile can be produced in a highest yield in accordance with the method of the present invention is relatively low, namely, about 400° C, thus creating an industrial advantage.

3. Since the optimum contact time of the reaction feed with the catalyst of the present invention, in which period acrylonitrile can be produced in a highest yield, is shorter than that of the conventional method using the old Mo—Co—Fe—Bi—O type catalyst, the space time yield of acrylonitrile is very high, namely, 250 g/l · hr or more.

4. Since only a small amount of bismuth is sufficiently needed in the catalyst of the present invention, the cost of the catalyst is relatively low.

Accordingly, the method of the present invention can produce acrylonitrile from propylene with a high industrial benefit.

In the new type of catalyst of the present invention, it is necessary that the atomic ratio $a:b:c:d:e$ is within the range of 10:3 to 10:1 to 7:0.1 to 1. If a catalyst is used in which the amounts of the contents of molybdenum, cobalt, iron, and bismuth are outside the above-specified range, both the percentages of selectivity to acrylonitrile and the conversion of propylene will decrease. Especially, the percentage of selectivity to acrylonitrile becomes remarkably decreased. These conditions results in a low yield of acrylonitrile.

If the catalyst contains vanadium or tellurium in an atomic ratio higher than the above-mentioned upper limit of 1, both percentages of selectivity to and yield of acrylonitrile will decrease. If the atomic ratio of vanadium or tellurium in the catalyst is lower than the specified lower limit of 0.01, the catalytic activity of the catalyst will be insufficiently small and the yield of acrylonitrile will become undesirably lower.

In the new type of catalyst of the present invention, the elements of the ingredient exist in the form of oxides thereof. Some of the oxides may form a complex. A plurality of said elements may form a compound together with oxygen.

In the preparation of the catalyst, the compounds containing the ingredient elements of the catalyst may be in the forms of oxides, hydroxides, salts, or acids. The salts are preferably capable of being thermally decomposed. The molybdenum-containing compound may be selected from molybdic acid, ammonium molybdate, molybdenum trioxide, phosphomolybdic acid, ammonium phosphomolybdate and molybdenum sulfide.

The cobalt-containing compound may be selected from cobalt carbonate, cobalt nitrate, cobalt (II) oxide, cobalt (III) oxide, cobalt chloride, tricobalt tetroxide, cobalt (II) hydroxide, cobalt (III) hydroxide, and cobalt sulfide.

The iron-containing compound may be selected from ferrous nitrate, ferric nitrate, ferrous oxide, ferric oxide, ferrous chloride, ferric chloride, ferrous hydroxide, ferric hydroxide, ferric phosphate, iron sulfides, ferrous sulfate and ferric sulfate.

The bismuth-containing compound may be selected from bismuth chloride, bismuth nitrate, bismuth oxide, bismuth oxychloride, bismuth hydroxide and bismuth subnitrate.

The vanadium-containing compound may be selected from vanadium pentaoxide, vanadium tetrachloride, ammonium metavanadate, vanadyl oxalate and vanadyl nitrate.

The tellurium-containing compound may be selected from ortho-telluric acid, meta-telluric acid, tellurium dioxide, tellurium dichloride, tellurium dioxalate and tellurium nitrate.

Materials containing two or more elements selected from molybdenum, cobalt, iron, bismuth, vanadium and tellurium, for example, cobalt molybdate and iron molybdate, may be used for the preparation of the catalyst of the present invention.

There are no limitations to the preparation methods of the catalyst of the present invention. Generally, the catalyst can be prepared by providing an aqueous mixture containing a molybdenum-containing compound, a cobalt-containing compound, an iron-containing compound, a bismuth-containing compound and at least one member selected from vanadium- and tellurium-containing compounds; converting the aqueous mixture into a dried solid mixture; and calcining the dried solid mixture at a temperature of at least 500° C.

For example, in the catalyst of the present invention consisting of molybdenum, cobalt, iron, bismuth, vanadium and oxygen, the aqueous mixture of the ingredient compounds may be prepared by the following process.

First, a solution is prepared by dissolving, a predetermined amount of a water-soluble molybdenum compound, for example, molybdic acid and ammonium molybdate and a predetermined amount of a water-soluble vanadium compound, for example, ammonium metavanadate and vanadyl nitrate, in a predetermined amount of hot water at a temperature of 50° to 90° C. Secondly, a solution is prepared by dissolving predetermined amounts of a water-soluble cobalt compound, for example, cobalt nitrate and cobalt chloride, and a water-soluble iron compound, for example, ferric nitrate and ferrous nitrate, in a predetermined amount of water. Thirdly, an acid solution is provided by dissolving a predetermined amount of a water-soluble bismuth compound, for example, bismuth nitrate and bismuth hydroxide, in a predetermined amount of water and acidifying the solution with nitric acid. The second and third solutions are poured dropwise into the first solution while stirring the solution. An aqueous slurry mixture containing the catalytic ingredient compounds is obtained.

In the preparation of the aqueous mixture of the ingredient compound, it is preferable that the compounds containing molybdenum, cobalt and iron which are contained in large amounts in the catalyst, be water-soluble because water-soluble compounds can be uniformly mixed in an aqueous mixture.

In the preparation of the catalyst, the conversion of the aqueous mixture into the solid mixture may be carried out by way of evaporation. Alternatively, the aqueous mixture may be subjected to a precipitation treatment by which all of the ingredient element-containing compounds are precipitated. The precipitate is separated from the mixture by way of filtering or centrifugalizing and then dried.

The solid mixture thus prepared may be calcined at a temperature of at least 500° C for a period of time sufficient enough for converting the solid mixture into an activated catalyst. The calcining temperature is preferably in a range from 500° to 700° C, more preferably, from 530° to 670° C. A calcining temperature lower than 500° C, will tend to reduce the percentage of selectivity to acrylonitrile. This will result in a low yield of acrylonitrile.

A calcining temperature higher than 700° C will tend to decrease the percentage of conversion of propylene. This will also result in a low yield of acrylonitrile.

The above-mentioned catalyst of the present invention may be used alone. However, in order to improve the mechanical strength of the catalyst, it is preferable that the catalytic ingredient be supported on a carrier. The carrier may consist of any type of conventional carrier materials. However, it is preferable that the carrier consists of at least one material selected from the group consisting of silica, alumina, silica-alumina, titania and silicates. It is preferable that the ratio by weight of the catalyst to the carrier is 1:0.01 to 3.0, more preferable, 1:0.1 to 2.0.

There is no limitation to the size and form of the catalyst. That is, the catalyst of the present invention can be screened into a desired size and can be formed into a desired form, for example, powder, grains, granules, pellets or tablets having a desired rigidity, depending upon the purpose and conditions under which the catalyst is to be used. Further, it should be noted that the formation of the catalyst results in no change in the catalytic activity of the catalyst.

In the method of the present invention, the reaction feed comprises propylene, ammonia and molecular oxygen. This reaction feed can be prepared by mixing a propylene source in gas phase with ammonia and a molecular oxygen-containing gas. The molecular oxygen-containing gas may be an industrially pure oxygen gas. However, it is not required that the molecular oxygen-containing gas have a particularly high concentration of oxygen. Accordingly, the molecular oxygen-containing gas may be air, which is economically advantageous.

The propylene source to be used in the method of the present invention is not required to have propylene of a high purity. However, it is preferable that the propylene be free from a certain type of compounds, for example, n-butylene and acetylene, which are reactive under the condition wherein propylene is catalytically converted.

In a preferable embodiment of the reaction feed of the present invention, the mole ratio of oxygen to propylene is in a range of 1 to 4:1, more preferably, 1.2 to 3:1, and the mole ratio of ammonia to propylene is in a range of 0.5 to 2.0:1, more preferably, 0.8 to 1.2:1. Further, it is preferable that the concentration of propylene in the reaction feed be in a range of 1 to 30% by volume, more preferably, 2 to 15% by volume.

The reaction feed can contain an inert diluent gas which does not affect the conversion of propylene into acrylonitrile, for example, nitrogen, carbon dioxide and steam. It is preferable that the proportion by mole of the inert diluent gas to propylene in the reaction feed to 0.1 to 30:1.

Especially, steam is effective for increasing not only the selectivity percentage of the aimed acrylonitrile but the durability in the catalytic activity of the catalyst. When steam is used as the diluent gas, it is preferable that the proportion by mole of the steam to propylene in the reaction feed be 0.1 to 5:1, more preferably, 0.5 to 4:1.

The method of the present invention can be effected under the same conditions as those common in the conventional ammoxidation reactions. In the method of the present invention, the reaction feed may come into contact with the catalyst under ambient pressure, slightly increased pressure or slightly reduced pressure. However, it is convenient that the contact be effected under an ambient pressure.

The reaction in the method of the present invention is carried out at an elevated temperature, preferably, in a range from 330° to 470° C, more preferably, from 350° to 450° C, still more preferably, from 380° to 420° C.

There is no limitation with regard to the contact time, as far as the desired oxidation is completed within said contact time. That is, the reaction of the present invention can be completed by flowing the reaction feed so as to contact the catalyst for 0.2 to 7 seconds, preferably, 0.5 to 4 seconds, still more preferably, for 1 to 3 seconds, under an ambient pressure.

The catalyst of the present invention may be used in a fluidized bed, moving bed or fixed bed. Especially, when the fixed bed is utilized in the method of the present invention, it is preferable that steam be added to the reaction feed, because continuation in the catalytic activity of the catalyst in the fixed bed is increased by the addition of steam.

The resultant acrylonitrile from the method of the present invention may be isolated from the reaction mixture by any conventional isolating method, for example, the methods disclosed in U.S. Pat. Nos. 3,424,781 and 3,688,002.

The specific examples, shown below will serve to more fully explain the practice of the method of the present invention. However, it should be understood that the examples are only illustrative and should in no way limit the scope of the present invention.

In the examples, the percentage of conversion of propylene, the percentage of selectivity to acrylonitrile and the percentage of yield of acrylonitrile were respectively calculated in accordance with the following equations:

conversion percentage of propylene $= X_1 - X_2/X_1 \times 100$, selectivity percentage to acrylonitrile $= Y/X_1 - X_2 \times 100$ and yield percentage of acrylonitrile $= Y/X_1 \times 100$ wherein $X_1$ denotes an amount by mole of propylene contained in the reaction feed prior to the start of the reaction, $X_2$ denotes an amount by mole of the unreacted propylene in the reaction mixture after the reaction, and Y denotes an amount by mole of the resultant acrylonitrile. Further, in the example, the space time yield of acrylonitrile was calculated in accordance with the following equation.

space time yield of acrylonitrile (g/l · hr) $= W/Z$ (l)

wherein W denotes an amount in gram of acrylonitrile produced in one hour and Z represents an amount in liter of a catalyst used. The space time yield of acrylonitrile is expressed in the dimensions of g/l · hr.

EXAMPLES 1 THROUGH 6 AND COMPARISON EXAMPLES 1 THROUGH 3

In Example 1, an aqueous slurry mixture of ingredients was provided by using the following procedures. First, 166.1 g of ammonium molybdate [$(NH_4)_6 \cdot Mo_7O_{24} \cdot 4H_2O$] and 0.55 g of ammonium metavanadate [$NH_4VO_3$] were dissolved in 250 ml of water which had been heated to a temperature of 80° C while stirring the solution. Secondly, 191.7 g of cobalt nitrate [$CO_2(NO_3)_2 \cdot 6H_2O$] and 76.1 g of ferric nitrate [$Fe(NO_3)_3 \cdot 9H_2O$] were dissolved in 200 ml of hot water at a temperature of 80° C. Thirdly, 9.12 g of bismuth nitrate [$Bi(NO_3)_3 \cdot 5H_2O$] were dissolved in 10 ml of an aqueous solution of 15% by weight of nitric acid. The second and third solutions were poured dropwise into the first solution while stirring the latter solution. An aqueous slurry mixture was obtained.

The slurry mixture was heated to a temperature of 200° C so as to form a dried solid mixture of the above-mentioned materials. The dried solid mixture was formed into tablets, each tablet having a diameter of 5 mm and a thickness of 5 mm, said tablets were heated to a temperature of 550° C at a heating-up rate of 50° C/hr and calcined at the above temperature for 5 hours in a calcining furnace. The resultant catalyst had an atomic ratio of the ingredient elements as shown in Table 1.

A reaction column was provided by charging 8 ml of the catalyst prepared above into an U-shaped glass tube having an inner diameter of 8 mm. The reaction column was heated to a temperature of 400° C and maintained at said temperature. A reaction feed which had been prepared by mixing in gas phase propylene, ammonia, air and steam in a mole ratio of 1.0:1.0:11.0:2.0 was passed through the reaction column rate of 282 ml/min. The reaction feed contacts the catalyst for 1.7 seconds under ambient pressure. In this reaction feed, the ratio by mole of oxygen to propylene was about 2.3:1.

In Example 2, the procedures identical to those in Example 1 were carried out, except that the amount of ammonium metavanadate used was changed to 1.1 g.

In Example 3, the same procedures as those in Example 1 were effected, except that ammonium metavanadate was used in an amount of 2.2 L g.

In Examples 4 through 6, the same procedures as those in Examples 2 were conducted, except that the bismuth nitrate was used in amounts of 6.84 g (Example 4), 13.68 g (Example 5) and 18.24 g (Example 6), respectively.

In Comparison Example 1, the same procedure as in Example 1 were repeated, except that no ammonium metavanadate was used in the production of the catalyst.

In Comparison Example 2, procedures identical to those in Example 3 were repeated, except that no ammonium metavanadate was employed in the preparation of the catalyst.

In Comparison Example 3, the same operations as in Example 5 were conducted, except that ammonium metavanadate was used in an amount of 22 g in place of 1.1 g. The content of vanadium in the resultant catalyst was outside the specified scope of the vanadium content in the catalyst of the present invention.

Table 1 shows the atomic ratios of the ingredient elements in the resultant catalysts of the above examples and comparison examples. Table 1 also shows the percentages of conversion of propylene, selectivity to acrylonitrile, and yield of acrylonitrile and the space time yields of the acrylonitrile in the above-mentioned examples and comparison examples. Each of the above percentages and the space time yields of the acrylonitrile was determined from the results of the measurements taken 1 hour after the start of the reaction.

EXAMPLES 7 THROUGH 17

In Example 7, a catalyst was prepared by using the same procedures as those in Example 4, except that 2.16 g of telluric acid [$H_2TeO_4 \cdot 4H_2O$] were used in place of the ammonium metavanadate. The ammoxidation reaction was carried out by the same method as in Example 2.

In Example 8, the same operations as those in Example 2 were carried out except that, in the preparation of the catalyst, 2.16 g of telluric acid was employed instead of the ammonium metavanadate.

In Example 9, a catalyst was prepared by using the same method as that in Example 5, except that 2.16 g of telluric acid were used instead of the ammonium metavanadate, and the catalyst was used in the same ammoxidation reaction as that in Example 2.

In Examples 10 and 11, procedures identical to those in Example 2 were conducted, except that the calcining temperature was 600° C in Example 10 and 650° C in Example 11.

In Examples 12 and 13, procedures identical to those in Example 2 were effected, except that the ammoxidation reaction was effected at temperatures of 380° C in Example 12 and 420° C in Example 13.

In Examples 14 and 15, the same operations as those in Example 2 were carried out, except that the cobalt nitrate was employed in amounts of 137 g in Example 14 and 219.2 g in Example 15.

In each of the Examples 16 and 17, the same process as that in Example 2 was conducted, except for the changing of the amounts of ferric nitrate used from 76.1 g to 57.08 g in Example 16 and to 114.15 g in Example 17, respectively.

The results in Examples 7 through 17 are shown in Table 2.

Table 1

| Example No. | | Atomic ratio of the elements of the ingredient | | | | Conversion percentage of propylene | Selectivity percentage to acrylonitrile | Yield percentage of acrylonitrile | Space time yield of acrylonitrile (g/l . hr) |
|---|---|---|---|---|---|---|---|---|---|
| | | Mo | Co | Fe | Bi | V | | | |
| Example | 1 | 10 | 7 | 2 | 0.2 | 0.05 | 96.3 | 84.2 | 81.0 | 271 |
| | 2 | 10 | 7 | 2 | 0.2 | 0.1 | 98.1 | 84.7 | 83.1 | 278 |
| | 3 | 10 | 7 | 2 | 0.2 | 0.2 | 98.3 | 83.9 | 82.5 | 276 |
| | 4 | 10 | 7 | 2 | 0.15 | 0.1 | 97.8 | 84.3 | 82.4 | 276 |
| | 5 | 10 | 7 | 2 | 0.3 | 0.1 | 98.6 | 83.4 | 82.2 | 275 |
| | 6 | 10 | 7 | 2 | 0.4 | 0.1 | 98.8 | 80.0 | 79.0 | 264 |
| Comparison Example | 1 | 10 | 7 | 2 | 0.2 | — | 82.9 | 81.2 | 67.3 | — |
| | 2 | 10 | 7 | 2 | 0.3 | — | 81.7 | 80.3 | 65.6 | — |
| | 3 | 10 | 7 | 2 | 0.3 | 2 | 98.7 | 51.6 | 50.9 | — |

Table 2

| Example No. | Atomic ratio of the elements in the ingredient | | | | | | Calcining temperature (° C) | Reaction temperature (° C) | Conversion percentage of propylene | Selectivity percentage to acrylonitrile | Yield percentage of acrylonitrile |
|---|---|---|---|---|---|---|---|---|---|---|---|
| | Mo | Co | Fe | Bi | V | Te | | | | | |
| 7 | 10 | 7 | 2 | 0.15 | — | 0.1 | 550 | 400 | 94.8 | 85.2 | 80.8 |
| 8 | 10 | 7 | 2 | 0.2 | — | 0.1 | 550 | 400 | 96.0 | 85.3 | 81.5 |
| 9 | 10 | 7 | 2 | 0.3 | — | 0.1 | 550 | 400 | 94.3 | 84.9 | 80.1 |
| 10 | 10 | 7 | 2 | 0.2 | 0.1 | — | 600 | 400 | 95.8 | 85.1 | 81.5 |
| 11 | 10 | 7 | 2 | 0.2 | 0.1 | — | 650 | 400 | 92.2 | 85.6 | 78.9 |
| 12 | 10 | 7 | 2 | 0.2 | 0.1 | — | 550 | 380 | 93.4 | 84.8 | 79.2 |
| 13 | 10 | 7 | 2 | 0.2 | 0.1 | — | 550 | 420 | 99.2 | 81.7 | 81.0 |
| 14 | 10 | 5 | 2 | 0.2 | 0.1 | — | 550 | 400 | 96.8 | 84.1 | 81.4 |
| 15 | 10 | 8 | 2 | 0.2 | 0.1 | — | 550 | 400 | 98.7 | 83.9 | 82.8 |
| 16 | 10 | 7 | 1.5 | 0.2 | 0.1 | — | 550 | 400 | 97.3 | 84.0 | 81.7 |
| 17 | 10 | 7 | 3 | 0.2 | 0.1 | — | 550 | 400 | 98.4 | 84.2 | 82.9 |

EXAMPLES 18 AND 19

In Example 18, an aqueous slurry mixture was prepared by using the same procedures as those in Example 2. The resultant aqueous slurry mixture was admixed with 118 g of an aqueous solution containing 30% by weight of silica sol. The aqueous admixture thus obtained was evaporated at a temperature of 200° C to convert said admixture from an aqueous to a solid admixture. The solid admixture was formed into tablets of the same size as those in Example 1. The tablets were heated to a temperature of 550° C at a heating-up rate of 50° C/hr, and calcined at the above temperature for 5 hours to provide a catalyst-carrier composition. The ratio by weight of the carrier to the catalyst is shown in Table 2. The same ammoxidation reaction as in Example 2 was effected by using 8 ml of the above-prepared catalyst-carrier composition.

In Example 19, the same process as in Example 18 was conducted except that the aqueous solution of the silica sol was used in an amount of 236 ml.

The results are indicated in Table 3.

Table 3

| Example No. | Ratio by weight of carrier to catalyst (%) | Conversion percentage of propylene | Selectivity percentage to acrylonitrile | Yield percentage of acrylonitrile |
|---|---|---|---|---|
| 18 | 20 | 99.0 | 84.1 | 83.3 |
| 19 | 40 | 98.2 | 84.3 | 82.8 |

What we claim is:

1. A process for the catalytical preparation of acrylonitrile, comprising bringing, at an elevated temperature, a reaction feed containing propylene, ammonia and molecular oxygen in gas phase into contact with a catalyst consisting of an oxide composition of the empirical formula:

$$Mo_aCo_bFe_cBi_dX_eO_f$$

wherein X represents at least one atom of an element selected from vanadium and tellurium, the subscripts $a$, $b$, $c$, $d$, $e$ and $f$ respectively denote the numbers of the respective atoms of the elements, the ratio $a:b:c:d:e$ being in the range of 10:3 to 10:1 to 7:0.1 to 0.7:0.01 to 1; and the subscript $f$ represents the number of oxygen atoms which satisfies the average valency of the elements, the ratio $a:f$ being in the range of 10:34.6 to 54.1.

2. A method as claimed in claim 1, wherein said contact is effected at a temperature of 330° to 470° C.

3. A method as claimed in claim 2, wherein said contact temperature is in a range from 350° to 450° C.

4. A method as claimed in claim 3, wherein said contact temperature is in a range of 380° to 420° C.

5. A method as claimed in claim 1, wherein said contact is carried out for 0.2 to 7 seconds.

6. A method as claimed in claim 5, wherein said contact time is in a range from 0.5 to 4 seconds.

7. A method as claimed in claim 6, wherein said contact time period is in a range from 1 to 3 seconds.

8. A method as claimed in claim 1, wherein said reaction feed contains an inert diluent gas.

9. A method as claimed in claim 8, wherein the proportion in content by mole of the diluent gas to propylene in the reaction feed is 0.1 to 30:1.

10. A method as claimed in claim 8, wherein said diluent gas is selected from steam, nitrogen and carbon dioxide.

11. A method as claimed in claim 10, wherein the proportion by mole of the steam to the content of propylene in the reaction feed is 0.1 to 5:1.

12. A method as claimed in claim 11, wherein the proportion by mole of steam to propylene in the reaction feed is 0.5 to 4:1.

13. A method as claimed in claim 1, wherein the source of said molecular oxygen to be present in said reaction feed in either pure oxygen gas or air.

14. A method as claimed in claim 1, wherein the source of said propylene to be present in said reaction feed is free from n-butylene and acetylene.

15. A method as claimed in claim 1, wherein the mole ratio of oxygen to propylene to be present in said reaction feed is in a range of 1 to 4:1.

16. A method as claimed in claim 15, wherein said mole ratio of oxygen to propylene is in a range of 1.2 to 3:1.

17. A method as claimed in claim 1, wherein the mole ratio of ammonia to propylene to be present in said reaction feed is in a range of 0.5 to 2.0:1.

18. A method as claimed in claim 17, wherein said mole ratio of ammonia to propylene is in a range of 0.8 to 1.2:1.

19. A method as claimed in claim 1, wherein said propylene is present in a concentration of 1 to 30% by volume in said reaction feed.

20. A method as claimed in claim 19, wherein said concentration of propylene is said reaction feed is 2 to 15% by volume.

21. A method as claimed in claim 1, wherein said catalyst is borne on a carrier selected from silica, alumina, silica-alumina, titania and silicates.

22. A method as claimed in claim 19, wherein the ratio by weight of said carrier to said catalyst is 0.01 to 3:1.

23. A method as claimed in claim 22, wherein said ratio by weight of said carrier to said catalyst is 0.1 to 2:1.

24. A method as claimed in claim 1, wherein said catalyst is prepared by providing an aqueous mixture containing a molybdenum-containing compound, a cobalt-containing compound, an iron-containing compound, a bismuth-containing compound and at least one member selected from vanadium- and tellurium-containing compounds; converting said aqueous mixture into a dried solid mixture; and calcining said dried solid mixture at a temperature of at least 500° C.

25. A method as claimed in claim 24, wherein said calcining temperature is in a range of from 500° to 700° C.

26. A method as claimed in claim 1, wherein said X in the empirical formula is vanadium.

27. A method as claimed in claim 1, wherein said X in the empirical formula is tellurium.

* * * * *